United States Patent
Bowald et al.

[11] Patent Number: 5,423,865
[45] Date of Patent: Jun. 13, 1995

[54] ELECTRODE SYSTEM FOR A DEFIBRILLATOR

[75] Inventors: Staffan Bowald, Almunge; Jakub Hirschberg, Taeby; Jens Wolf, Johaneshov, all of Sweden

[73] Assignee: Siemens Elema AB, Solna, Sweden

[21] Appl. No.: 161,408

[22] Filed: Dec. 6, 1993

[30] Foreign Application Priority Data

Dec. 11, 1992 [SE] Sweden ............... 9203732

[51] Int. Cl.[6] ............... A61N 1/39
[52] U.S. Cl. ............... 607/5; 607/122; 607/126
[58] Field of Search ............... 607/5, 123, 122, 119, 607/116, 126; 604/104

[56] References Cited

U.S. PATENT DOCUMENTS

| | | |
|---|---|---|
| 4,708,145 | 11/1987 | Tacker, Jr. et al. |
| 4,727,877 | 3/1988 | Kallok |
| 4,825,871 | 5/1989 | Cansell ............... 607/5 |
| 5,014,696 | 5/1991 | Mehra |
| 5,044,375 | 9/1991 | Bach, Jr. et al. |
| 5,107,834 | 4/1992 | Ideker et al. ............... 607/5 |
| 5,221,261 | 6/1993 | Termin et al. ............... 604/104 |
| 5,235,977 | 8/1993 | Hirschberg et al. |
| 5,256,146 | 10/1993 | Ensminger et al. ............... 604/104 |

FOREIGN PATENT DOCUMENTS

WO92/11898 7/1992 WIPO.

*Primary Examiner*—William E. Kamm
*Assistant Examiner*—Kennedy J. Schaetzle
*Attorney, Agent, or Firm*—Hill, Steadman & Simpson

[57] ABSTRACT

An electrode system for a defibrillator avoids the use of a ventricular electrode, and provides efficient utilization of the energy stored in the defibrillator with a beneficial distribution of current in the heart. The electrode system includes three electrodes, at least two of which are intravascular electrodes. One of these intravascular electrodes is placed in the inferior vena cava and the other is placed in the coronary sinus, including its continuation (the great cardiac vein) along the base of the heart. The third electrode can be either an extravascular patch electrode, located in the region of the left ventricle, or an additional intravascular electrode located in the superior vena cava. The intravascular electrodes are devised so that they do not impede the flow of blood in the vein in which they are located.

16 Claims, 3 Drawing Sheets

ELECTRODE SYSTEM FOR A DEFIBRILLATOR

BACKGROUND OF THE INVENTION

1. Field of the Invention

The present invention relates generally to an electrode system intended for proximal connection to a cardioverter/defibrillator, and for distal placement in the heart region for delivering electrical energy from the cardioverter/defibrillator to the heart, for effectively terminating an arrhythmia in the heart. More specifically, the invention relates to such an electrode system having three electrodes, at least two of which are intravascular electrodes.

2. Description of the Prior Art

Defibrillation/cardioversion systems ("cardioversion" in this context referring to defibrillation using lower energy; the generic designation "defibrillation" will henceforth be used below) are known employ a three-electrode system, with two of the electrodes being intravascular electrodes. One of the intravascular electrodes is normally placed in the right ventricle and the other is placed either in the superior vena cava or, less commonly, in the inferior vena cava or in the coronary sinus and its continuation (the great cardiac vein) along the base of the heart. The third electrode in known systems is a subcutaneous electrode with a large area, i.e., a patch electrode. For the purpose of achieving efficient energy utilization of the energy stored in the heart and a good distribution of current in the heart, while simultaneously avoiding major surgery such as opening of the thorax, the subcutaneous patch electrode is usually placed in the vicinity of the left ventricle, between the thorax and the skin.

Electrode systems with the above-described electrode locations are described in a number patents, including U.S. Pat. No. 4,708,145. This patent discloses intravascular electrodes with a common electrode cable for a plurality of electrodes in the right ventricle and superior vena cava. It is also known to provide separate electrode cables for different electrodes, as well as a separate sensing electrode for detecting cardiac events, as described in U.S. Pat. No. 4,727,877, European Application 0 373 953, corresponding to U.S. Pat. No. 5,014,686 and U.S. Pat. No. 5,044,375.

A common feature of prior art electrode systems is the adaptation of one of the electrodes for placement in the right ventricle, and placement of that electrode in the right ventricle. Such an endocardiac electrode imposes strain on the heart in the form of irritation of the musculature of the heart wall and the valves between the atrium and ventricle, as discussed in European Application 92 104 098, corresponding to U.S. Pat. No. 5,235,977. There is also an associated increased risk of blood formation. Therefore, an electrode system is disclosed in European Application 92 104 098 wherein the endocardiac electrode is avoided, and is replaced by an electrode in the inferior vena cava.

SUMMARY OF THE INVENTION

It is an object of the present invention to provide an electrode system for a defibrillator which avoids the use of a ventricular electrode, and which achieves efficient utilization of the energy stored in the defibrillator together with a favorable distribution of current in the heart. The above object is achieved in accordance with the principles of the present invention in an electrode system for a defibrillator having three electrodes, at least two of which are intravascular electrodes, with one of the intravascular electrodes being adapted for placement in the inferior vena cava. The third electrode can be either a patch electrode, which can be placed in the region of the left ventricle, or an additional intravascular electrode adapted for placement in the superior vena cava. The other of the two intravascular electrodes is adapted for placement in the coronary sinus, including its continuation (the great cardiac vein) along the base of the heart.

The electrode system constructed in accordance with the principles of the present invention attains a three-electrode system without the use of a ventricular electrode, and having at least two intravascular electrodes, one of which is adapted for placement in the coronary sinus, including its continuation along the base of the heart.

A method for defibrillating a heart with a three-electrode system is also disclosed, including the steps of placing one electrode in the inferior vena cava, placing another electrode in the coronary sinus including its continuation along the base of the heart, and placing a third electrode either, in the form of a patch electrode, in the region of the left ventricle, or in the form of intravascular electrode, in the superior vena cava.

In a further embodiment of the invention, at least some of the venous electrodes can be connected by a common electrode cable. The venous electrodes may also carry means for fixing the electrodes to the inner venous wall. The fixing means can be in the form of a hollow, resilient cylinder, with fixing being achieved by radially expanding the cylinder. The hollow cylindrical shape of the electrode enables blood to flow unimpeded through the electrode.

DESCRIPTION OF THE PREFERRED EMBODIMENTS

Figure 1:
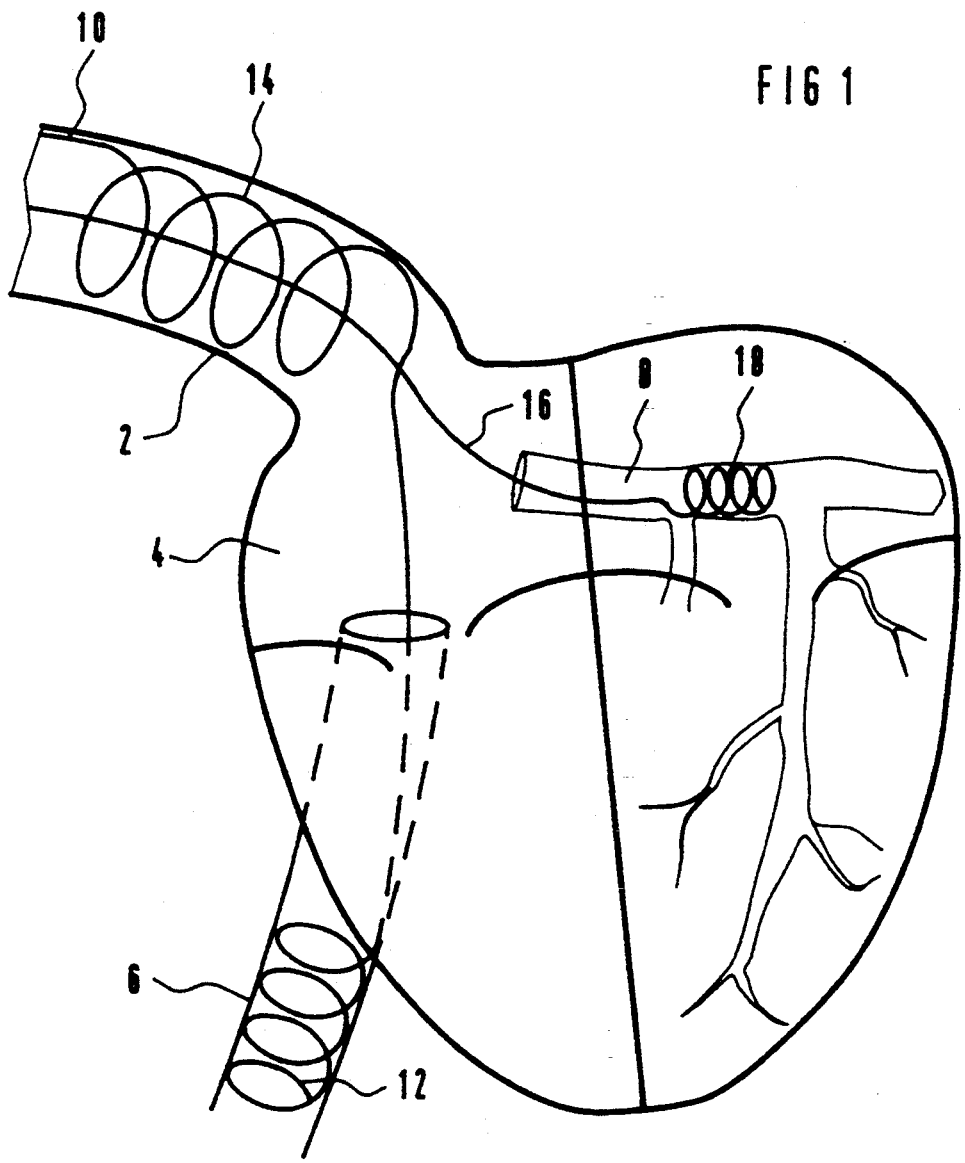
FIG. 1 is a schematically represented cross-section of a heart (frontal plane) for illustrating a first embodiment of an electrode system constructed in accordance with the principles of the present invention.
Figure 2:
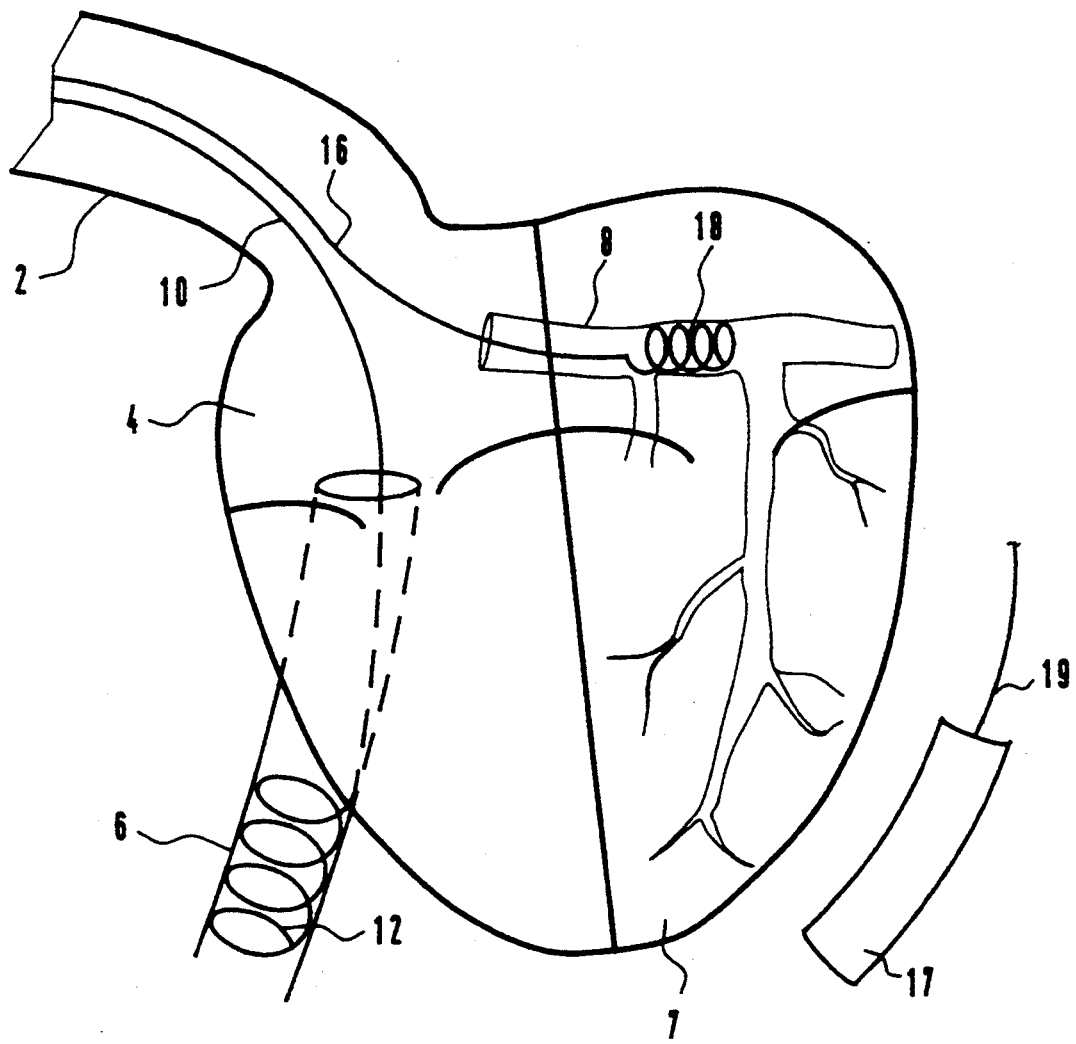
FIG. 2 is a schematically represented cross-section of a heart (frontal plane) for illustrating a second embodiment of an electrode system constructed in accordance with the principles of the present invention.

FIGS. 1 and 2 respective show first and second embodiments of an electrode system constructed in accordance with the principles of the present invention, wherein the same or similar components are designated with identical reference numerals. Hidden electrode components in the inferior vena cava, as well as a portion of the inferior vena cava itself, are shown with dashed lines.

FIG. 1 is a schematic representation of a cross-section of a human heart, together with a number of vessels of relevance to the invention. A first electrode cable 10 is introduced through the superior vena cava 2, and passes through the right atrium 4 and exits into the inferior vena cava 6. At its distal end, the cable 10 carries an electrode 12 anchored in the inferior vena cava 6. The cable 10 also carries an additional electrode 14 anchored in the superior vena cava 2 proximal to the electrode 12. A second electrode cable 16 is also introduced through the superior vena cava 2, but passes through the right atrium 4, in contrast to the cable 10, in such a manner that it exits into the coronary sinus 8 and its continuation, the great cardiac vein, along the base of the heart. At its distal end, the cable 16 carries an electrode 18 anchored in the coronary sinus/great cardiac vein 8. The electrode 18 is connectable to a defibrillator 20 by a connector which is present in the cable 16. The electrodes 12 and 14 are also individually connected to the defibrillator 20 by separate conductors which are present in the cable 10.

Figure 3:
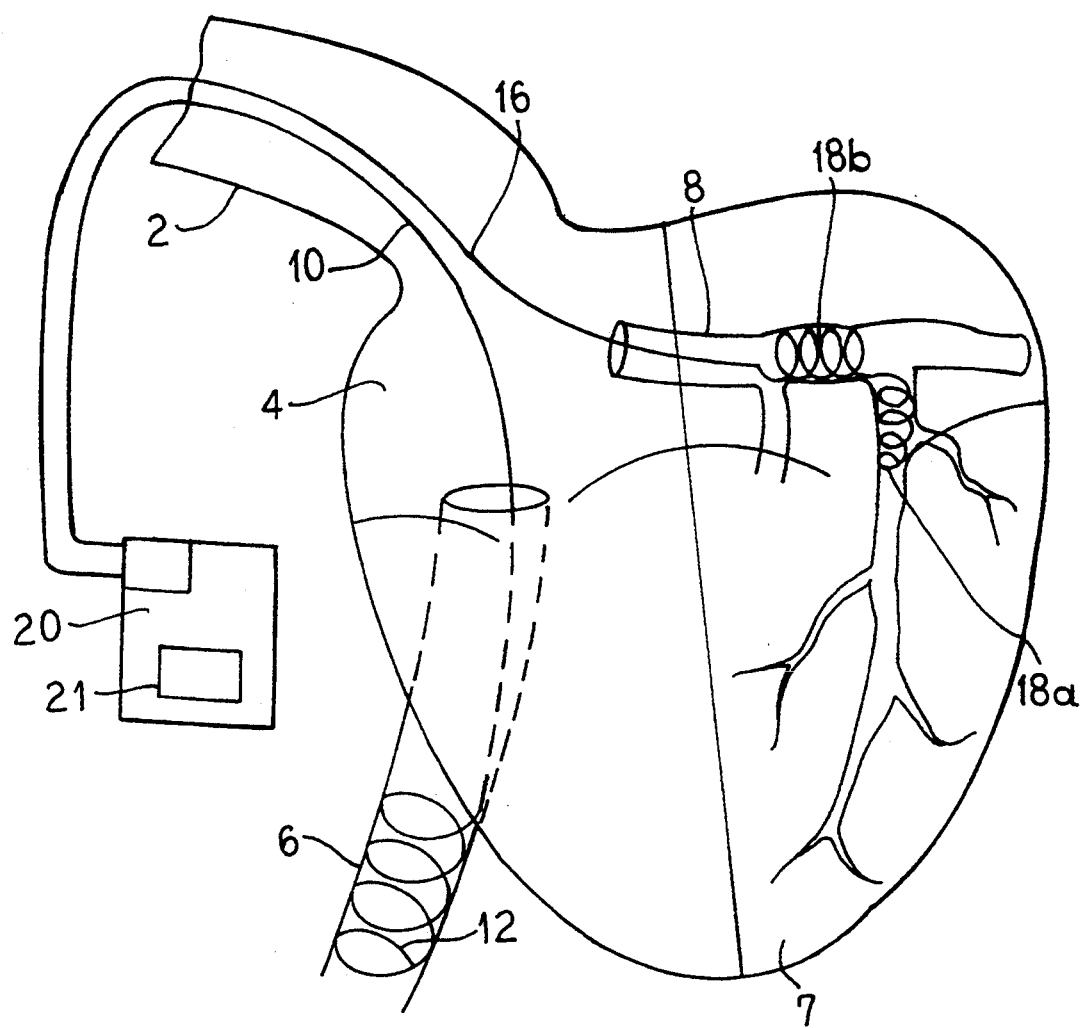
FIG. 3 is a schematically represented cross-section of a heart (frontal plane) for illustrating a third embodiment of an electrode system constructed in accordance with the principles of the present invention.

The electrode system shown in FIG. 2 differs from the system shown in FIG. 1 by substitution of the electrode 14 sited in the superior vena cava 2 with a subcutaneous patch electrode 17 placed near the left ventricle 7. The patch electrode 17 is connectable to the defibrillator by a conductor carried in the cable 19. As used herein, "subcutaneous placement" means placement between the thorax (including the ribs) and the skin. The implantable housing 20 of the defibrillator can alternatively be employed as a patch electrode (see FIG. 3).

Connection of the electrodes to the defibrillator according to the embodiments of FIGS. 1 and 2, as well as connections between certain of the electrodes, can be achieved in different ways. For example, the electrodes 14 and 18 in the embodiment of FIG. 1 can be interconnected so that the defibrillation pulse is emitted between (across) these electrodes, as well as between (across) these electrodes and the electrode 12 in the inferior vena cava 6. In a corresponding manner, the electrodes 17 and 18 in FIG. 2 can be interconnected so that the alefibrillation pulse is emitted between these electrodes, as well as between these electrodes and the electrode 12.

The electrodes 12, 14 and 18 in the embodiment of FIG. 1, and the electrodes 12, 17 and 18 in the embodiment of FIG. 2 can alternatively be interconnected such that the defibrillation pulse is emitted only between one of these electrodes and the other two electrodes. Alternatively, the electrodes 12, 14 and 18 and the electrodes 12, 17 and 18 can respectively be supplied with different defibrillation voltages. As a further alternative, different pairs of electrodes within the three-electrode combination can deliver defibrillation pulses sequentially. Monophasic, biphasic or multiphasic defibrillation pulses can be used.

The cable 10 shown in FIG. 1, which is common to the two electrodes 12 and 14, can be replaced with separate electrode cables for these two electrodes 12 and 14. Another alternative is to introduce the intravascular electrodes through the inferior vena cava 6 instead of through the superior vena cava 2. As noted above for the introduction of the electrodes through superior vena cava 2, the intravascular electrodes, if introduced through the inferior vena cava 6, can have a common electrode cable or separate electrode cables. Thus, the electrodes 12 and 18 can alternately have a common electrode cable in both of the configurations shown in FIG. 1 and FIG. 2.

The above-described electrode configurations can be complemented with a separate stimulation/sensing electrode for stimulating/sensing cardiac events and/or with a sensor for different parameters related, for example, to cardiac hemodynamics. The sensing electrode cable can also contain a stimulation electrode for pacing functions.

The intravascular electrodes 12, 14 and 18 are maintained in place in their respective veins by virtue of being constructed so as to be radially expandable. The electrodes 12, 14 and 18 form at least the contours (surface configuration) of a hollow cylinder in their expanded state. Defibrillation electrodes of this type are described in applicants' co-pending application filed simultaneously herewith entitled "Defibrillation Electrode," Bowald et al., Ser. No. 08/161,412. The teachings of that co-pending application are incorporated herein by reference so as to avoid duplication. The intravascular electrodes 12, 14 and 18 are therefore maintained in place in their respective veins by being shaped as a helix, so as to apply slight pressure to the inner wall of the vein. For this purpose, the respective helices forming the intravascular electrodes 12, 14 and 18 are biased perpendicular to the longitudinal axis of the helix. To avoid repetition, only the helical fixing of the electrode 12 in the inferior vena cava 6 will be described individually, but the description applies as well to the other intravascular electrodes.

In its pre-shaped (pre-implantation) state, the helical electrode 12 can be envisioned as coiled around an imaginary cylinder having an external diameter slightly larger than the internal diameter of the inferior vena cava 6. The helix can be made of an electrically conductive, bio-compatible material. The electrode 12 is connected to the electrode cable 10 so as to form a single unit therewith. A centrally arranged longitudinal channel, through which a stylet can be introduced, runs through the electrode 12 and electrode cable 10. During implantation, the electrode 12 is straightened using a stylet, the diameter of the electrode 12 thereby becoming smaller than the diameter of the blood vessels it is to traverse, enabling it to be advanced into the inferior vena cava 6. When the implanting physician has decided on an appropriate site for the electrode 12 in the inferior vena cava 6, the stylet is withdrawn, causing the electrode 12 to resume its pre-shaped helical configuration. The pressure of the helix against the venous wall maintains the helix in the desired position. In its affixed position, the electrode 12 forms a relatively large electrode surface pressing on the vascular wall. At the same time, the helical electrode 12 has the advantage of enabling blood in the vessel to flow unobstructed through the interior of the helix. The risk of clot formation is thereby minimized. The electrode 12 can be readily repositioned by reintroduction of the stylet into the central channel, so as to straighten the electrode 12. The implanting physician can therefore easily find a site for the electrode 12 which, in combination with the other electrodes, achieves a favorable distribution of current in the heart tissue.

During implantation, the physician can employ an introductory catheter instead of a stylet. The electrode cable 10 with the straightened electrode 12 is then inserted into the introductory catheter, the introductory catheter being sufficiently stiff to maintain the electrode 12 in its straightened form during implantation. When the electrode 12 has been advanced to the desired position in the inferior vena cava 6, the introductory catheter is then withdrawn so that the electrode resumes its preformed configuration.

In those instances wherein the electrodes are carried on a common electrode cable, such as electrodes 12 and 14 in FIG. 1, the implantation can be performed using a single stylet in a central channel running along the length of the electrodes 12 and 14 and the cable 10. Both electrodes 12 and 14 are then straightened for implantation. When the electrode 12 reaches its desired position, the stylet is withdrawn enough for the electrode 12 to resume its helical configuration. The electrode 14 is then positioned at the desired site in the superior vena cava 2. When the electrode 14 is in its correct position, the stylet is completely withdrawn so that the electrode 14 also resumes its original, pre-shaped configuration. An introductory catheter can alternatively be used instead of the stylet, as described above.

The electrode 18 intended for location in the coronary sinus 8 and its continuation along the base of the heart can consist, for example, of two sub-electrodes 18a and 18b (see FIG. 3) respectively placed in the coronary sinus 8 and in its continuation, the great cardiac vein. The two sub-electrodes 18a and 18b can be arranged on a common electrode, for example, a continuation of the electrode cable 16. The two sub-electrodes are placed in the coronary sinus 8 and in the great cardiac vein such that an individually adapted, further improved distribution of current in the heart is achieved. Implantation is performed in the same way as described above. It is also possible to employ more than two sub-electrodes, as needed.

Although modifications and changes may be suggested by those skilled in the art, it is the intention of the inventors to embody within the patent warranted hereon all changes and modifications as reasonably and properly come within the scope of their contribution to the art.

We claim as our invention:

1. A system for administering defibrillation therapy to a heart comprising:
    a defibrillator which emits energy for defibrillating a heart;
    a first electrode connected to said defibrillator and adapted for placement in the inferior vena cava;
    a second electrode connected to said defibrillator and adapted for placement in the coronary sinus of said heart and its continuation along the base of said heart; and
    a third electrode connected to said defibrillator and adapted for non-ventricular placement relative to said heart for electrical interaction with said first and second electrodes in delivering said electrical energy to said heart.

2. An electrode system as claimed in claim 1 wherein said third electrode comprises a patch electrode adapted for subcutaneous placement in the region of the left ventricle.

3. An electrode system as claimed in claim 1 wherein said third electrode consists of an electrode adapted for placement in the superior vena cava.

4. An electrode system as claimed in claim 3 comprising a common electrode carrier carrying at least two of said first, second and third electrodes.

5. An electrode system as claimed in claim 3 wherein each of said first, second and third electrodes carries means for affixing the respective electrode to an inner wall of the vein in which the electrode is adapted for placement.

6. An electrode system as claimed in claim 5 wherein said means for fixing comprises a hollow-resilient cylinder having a diameter greater than the inner diameter of the vein in which the electrode is adapted for placement for pressing said electrode against said inner wall of said vein.

7. An electrode system as claimed in claim 6 wherein each of said first, second and third electrodes consist of a helix having winding defining a surface of said cylinder.

8. An electrode system as claimed in claim 1 for use with a defibrillator having a defibrillator housing and wherein said third electrode comprises a portion of said defibrillator housing.

9. An electrode system as claimed in claim 1 wherein said second electrode consists of at least two sub-electrodes including a distal sub-electrode and a proximal sub-electrode, said distal and proximal sub-electrodes being adapted for placement at respectively different sites within said coronary sinus and its continuation along the base of the heart, and further comprising a common electrode cable connecting said two sub-electrodes.

10. An electrode system as claimed in claim 1 further comprising a common electrode cable connecting said first and second electrodes.

11. An electrode system as claimed in claim 1 wherein each of said first and second electrodes carries means for affixing the electrode to an inner wall of the vein in which the electrode is adapted for placement.

12. An electrode system as claimed in claim 11 wherein said means for fixing comprises a hollow-resilient cylinder having a diameter greater than the inner diameter of the vein in which the electrode is adapted for placement for pressing said electrode against said inner wall of said vein.

13. An electrode system as claimed in claim 12 wherein each of said first, second and third electrodes consist of a helix having winding defining a surface of said cylinder.

14. A method for defibrillating a heart consisting of the steps:
    administering defibrillation therapy to a heart via an electrode system having first, second and third electrodes;
    placing said first electrode in the inferior vena cava;
    placing said second electrode in the coronary sinus and its continuation along the base of the heart; and
    placing the third electrode at a non-ventricular location relative to said heart for interacting with said first and second electrodes.

15. A method as claimed in claim 14 wherein said third electrode is a patch electrode, and wherein the step of placing said third electrode is further defined by subcutaneously placing said third electrode in the region of the left ventricle.

16. A method as claimed in claim 14 wherein said third electrode is an intravascular electrode, and wherein the step of placing said third electrode is further defined by placing said third electrode in the superior vena cava.

* * * * *